United States Patent
Leigh et al.

(10) Patent No.: US 8,612,012 B2
(45) Date of Patent: Dec. 17, 2013

(54) IMPLANTABLE HOUSING ASSEMBLY

(75) Inventors: C. Roger Leigh, East Ryde (AU); Mark Von Huben, Waverton (AU)

(73) Assignee: Cochlear Limited, Macquarie University, NSW (AU)

( * ) Notice: Subject to any disclaimer, the term of this patent is extended or adjusted under 35 U.S.C. 154(b) by 724 days.

(21) Appl. No.: 12/667,690

(22) PCT Filed: Jul. 2, 2008

(86) PCT No.: PCT/AU2008/000973
§ 371 (c)(1),
(2), (4) Date: Aug. 5, 2010

(87) PCT Pub. No.: WO2009/003235
PCT Pub. Date: Jan. 8, 2009

(65) Prior Publication Data
US 2010/0292760 A1  Nov. 18, 2010

(30) Foreign Application Priority Data

Jul. 2, 2007 (AU) .................. 2007903541
Jul. 2, 2007 (AU) .................. 2007903542
Jan. 3, 2008 (AU) .................. 2008900018

(51) Int. Cl.
*A61N 1/375* (2006.01)

(52) U.S. Cl.
USPC ............................ 607/57; 29/825; 174/520

(58) Field of Classification Search
USPC ............................ 607/57; 174/520; 29/825
See application file for complete search history.

(56) References Cited

U.S. PATENT DOCUMENTS

| | | | |
|---|---|---|---|
| 4,723,923 A * | 2/1988 | Senor et al. | 439/853 |
| 4,785,827 A * | 11/1988 | Fischer | 607/57 |
| 5,041,019 A | 8/1991 | Sharp et al. | |
| 5,103,818 A | 4/1992 | Maston et al. | |
| 5,282,841 A | 2/1994 | Szyszkowski | |
| 5,336,246 A | 8/1994 | Dantanarayana | |
| 5,683,435 A | 11/1997 | Truex et al. | |
| 6,011,993 A | 1/2000 | Tziviskos et al. | |
| 6,052,623 A | 4/2000 | Fenner et al. | |
| 6,272,382 B1 * | 8/2001 | Faltys et al. | 607/57 |
| 6,297,943 B1 | 10/2001 | Carson | |
| 6,505,073 B2 | 1/2003 | Gramse | |
| 6,721,602 B2 | 4/2004 | Engmark et al. | |
| 6,931,284 B2 * | 8/2005 | Engmark et al. | 607/36 |

FOREIGN PATENT DOCUMENTS

| | | |
|---|---|---|
| WO | 0203408 A2 | 1/2002 |
| WO | 2006081361 A2 | 8/2006 |

OTHER PUBLICATIONS

International Search Report. PCT/AU2008/000973. Mailed Aug. 29, 2008.

\* cited by examiner

*Primary Examiner* — Niketa Patel
*Assistant Examiner* — Alyssa M Alter
(74) *Attorney, Agent, or Firm* — Kilpatrick, Townsend & Stockton, LLP.

(57) ABSTRACT

Embodiments of the present invention relate to an implantable device housing assembly, for use in, for example, implantable prosthetic devices. In one aspect, the present invention provides a housing for an implantable device comprising a body portion and a sealing flange. The body portion includes a cavity in which electronic components are disposed on an open side thereof, and at least one feed-through which provides electrical connections between the electronic components and the exterior of the device. The feed-through includes interior and exterior connection points, which are accessible during assembly of the device from a first side of the device. The sealing flange operatively seals the cavity so as to form a sealed housing. A method of forming a sealed housing for an implantable device is also provided.

30 Claims, 7 Drawing Sheets

IMPLANTABLE HOUSING ASSEMBLY

CROSS-REFERENCE TO RELATED APPLICATIONS

This application is a national stage application under 35 USC §371 (c) of PCT Application No. PCT/AU2008/000973, entitled "IMPLANTABLE HOUSING ASSEMBLY," filed on Jul. 2, 2008, which claims priority from Australian Patent Application No. 2007903542, filed on Jul. 2, 2007 and claims priority from Australian Patent Application No. 2007903541, filed on Jul. 2, 2007 and claims priority from Australian Patent Application No. 2008900018, filed on Jan. 3, 2008. The entire disclosure and contents of the above applications are hereby incorporated by reference herein.

BACKGROUND

1. Field of the Invention

The present invention relates generally to implantable medical devices, and more particularly to, a housing for an implantable medical device.

2. Related Art

Devices are implanted in the body of a recipient for a variety of purposes including monitoring, heart defibrillation, drug delivery and as neural and organ prostheses. Such implantable devices generally include electronic components and other functional elements configured for a variety of purposes, including delivery of electrical stimulation or drugs, monitoring of parameters, communication with, or control of, other devices to store information, and communication via RF or other means.

Housing assemblies for implantable devices are required to be hermetically sealed and impervious to bodily fluids. This protects the recipient from any interactions with non-biocompatible materials used in the construction of the components housed inside the housing assembly, and from other adverse interactions with the sealed components. The housing also protects the functional components of the device from bodily fluids which could cause electrical short-circuits or otherwise lead to failure of the device.

Certain devices require one or more electrical connections between the interior of a device housing and elements exterior to the device housing. Hermetic enclosures for such devices are constructed from biocompatible materials, such as titanium or ceramic, and include a feed-through component. The function of the feed-through is to provide an electrically conductive path from inside the enclosure to outside the enclosure, typically for several separate conductors. If the housing is formed from titanium (or other conductive material), the conductors need to be insulated from the housing, as well as from each other. The feed-through also needs to maintain a hermetic enclosure while passing through the housing body. The feed-through is typically constructed from platinum conductors embedded in a ceramic carrier.

Conventional assembly of the hermetic enclosure to encase the electronics for traditional implant designs requires significant skilled labor input and numerous operations. Housings are currently typically made from multiple pieces and require the device to be inverted to facilitate connections. Such complex assembly is costly and does not facilitate automation and reliability within the assembly process.

For example, patent document WO 2006/081361 discloses an implantable medical device having a top and bottom shell, between which is enclosed a chassis. The chassis has functional components secured to it and is hermetically sealed to one of the shells. The chassis has a feed-through allowing input and output lines to pass into or out of the hermetic enclosure.

Furthermore, U.S. Pat. No. 6,011,993 discloses an implantable medical device made from an electronic subassembly hermetically sealed in a ceramic case filled with a potting material. The case is hollow with a closed end and an open end through which the electronic subassembly is inserted while the potting material in the case is still non-cured or in a quasi-fluid state. A header, to which the electronic subassembly is connected, is hermetically bonded to a band on the open end of the case thus hermetically sealing the medical device. The header has a plurality of electrical feed-through terminals for connecting to the electronic components on the subassembly. A particular disadvantage of such a device is the complex, highly skilled assembly required for its manufacture.

Additionally, U.S. Pat. No. 4,785,827 discloses a housing assembly for electronic circuitry that can be used subcutaneously. The housing comprises a container and base subassemblies each including a ceramic portion and a continuous metal sealing flange. The ceramic portion of the container subassembly is dish like and contains a cavity within which are housed electronic components. A plurality of electric leads are brazed to and extend from the container subassembly. The sealing flanges of the container and base subassemblies are then nested together and welded to close and seal the housing assembly. This assembly requires complex skilled assembly.

SUMMARY

In accordance with one aspect of the present invention, a housing for an implantable device is disclosed. The comprises: a body portion having a plurality of walls defining a cavity in which electronic components may be are disposed, the cavity having an opening to an exterior of the housing on a first side of the body portion; a feed-through disposed in a first of the plurality of walls to provide an through the first wall between the electronic components and the exterior of the device, the feed-through having interior and exterior connection points, the interior and exterior connection points being accessible during assembly of the device from the open side of the body portion; and a sealing flange operatively sealing the cavity so as to form a sealed housing.

In accordance with a second aspect of the present invention, a method of forming a sealed housing for an implantable device is disclosed. The method comprises: providing a body portion having a cavity for disposing electronic components on an open side thereof; providing at least one feed-through which provides electrical connections between the electronic components and the exterior of the device, the feed-through having interior and exterior connection points, the interior and exterior connection points being accessible from the open side of the cavity; inserting the electronic components into said cavity, and making the necessary electrical connections to said interior and exterior connection points; and attaching a sealing flange over the open side of the cavity so as to seal the cavity and thereby provide a sealed housing.

BRIEF DESCRIPTION OF THE DRAWINGS

An illustrative embodiment of the present invention will be described with reference to the accompanying figures, in which:

FIG. 4 is a partial top and partial cross-sectional view of the body portion shown in FIG. 1 prior to insertion of the feed-through;

FIG. 15 is an alternative housing having a single feed-through with a coil located at 180 degrees to the feed-through;

FIG. 16 is another alternative embodiment of a housing having a single feed-through with a coil located at 90 degrees to the feed-through;

DETAILED DESCRIPTION

Figure 1:
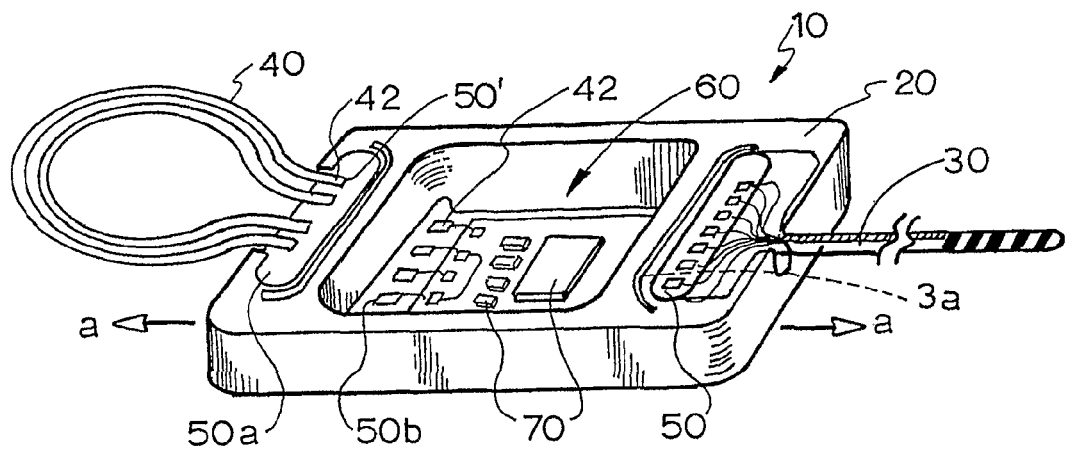
FIG. 1 is a perspective view of a body portion of a housing according to one embodiment of the present invention.

Aspects of the present invention are generally directed to a housing for an implantable device. The housing includes a feed-through disposed in a wall of the housing. The feed through includes internal and external electrical attachment points accessible from the same side of the housing. As such, embodiments of the present invention allow both electrical and mechanical assembly to occur from one single side of the housing.

In embodiments of the present invention, the interior and exterior connection points are made accessible from a single side of the housing by configuring the passage through the wall of the housing accordingly. This may illustratively be achieved by correctly angling a feed-through through a wall, or by using intersecting bores, passages and undercuts in the housing for carrying the feed-through. In one embodiment, access from a single side is achieved by at least part of the feed-through being generally parallel to a wall of the cavity, and providing access to the interior connection point through an undercut portion.

In embodiments of the present invention, at least one of the exterior component is integral with a feed-through conductor. In specific such embodiments, the feed-through is connected with an exterior component prior to its assembly or insertion into the housing. The exterior component may be selected from the group comprising a and an electrode array. However, it would be appreciated that the exterior component may also or any other electrical component. As noted above, embodiments of the present invention are directed to methods for manufacturing an implantable medical device. One exemplary method includes the steps of forming a feed-through assembly external of a housing. Such an exemplary feed-through assembly includes a feed-through and an exterior component connected thereto. The method further comprises subsequently inserting the feed-through assembly into the housing. Embodiments of the present invention are described herein primarily in connection with one type of implantable device, namely an implantable hearing prosthesis. Hearing prostheses in this sense include, but are not limited to, to any acoustic or electrical auditory stimulation devices, such as cochlear implants, middle ear implants, intra-cochlear array implants, brain stem implants, implantable mechanical stimulators, implantable acoustic devices or any combination thereof, such as a device that electrically and acoustically stimulates a recipient. However, it would be appreciated that embodiments of the present invention may be used in conjunction with any active implantable medical device in which it is necessary to provide an electrical connection from the exterior of the device to electrical or electronic components inside the device. It would be appreciated that such electrical connections may be used for a variety of purposes. In certain embodiments, such electrical connections may be used to connect internal electrical components with components outside the device used to, for example, record incoming signals, such as in a cardiac monitor, or for delivering electrical signals, such as in a pacemaker. Such electrical connections may also be used to connect a coil or similar device for transmission of RF power or data to internal electrical components It should also be appreciated that embodiments of the present invention are applicable to implantable devices which do not perform a medical function, such as, for example, identification or location devices.

FIG. 1 is a perspective view of the body portion 20 of a housing 10 in accordance with embodiments of the present invention. The illustrative housing 10 includes a body portion 20 having an opening or openings accessible on one side of the housing, and a sealing flange 80 (not shown in this view). The housing 10 shown is for use in a cochlear implant device, and as such is connected to a stimulation component, in the form of electrode array 30, at one end of the body portion 20. The housing 10 is connected to a coil 40 at the opposite end of the body portion 20.

As shown in FIG. 1, the body portion 20 includes two separate feed-throughs 50, 50' for the connection of electrode array 20 and coil 40, respectively, to an electronic assembly 70 disposed in cavity 60 of body portion 20. During assembly of the medical device, feed-throughs 50, 50' allow the formation of a connection between each of the coil 40 and electrode array 30 with electronics assembly 70 within the cavity 60 while accessing only a first one side (the top side as shown in FIG. 1) of body portion 20 in which the cavity is disposed. In other words, the feed-through interior connection point 50a (for making electrical connections between the electronic assembly 70 and the interior of the feedthrough) is accessible from the top of the body portion 20, as is the feed-through exterior connection point 50b (for making electrical connections between the feed-through and the components on the exterior of the device).

Figure 2:
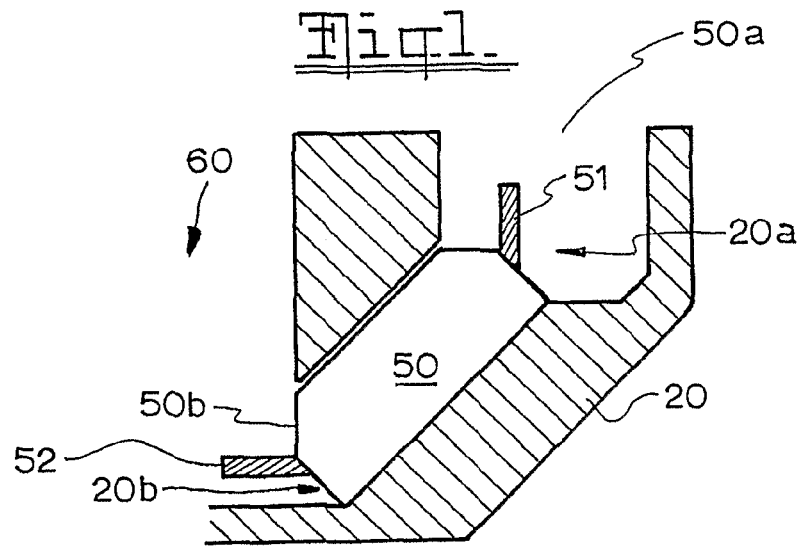
FIG. 2 is a partial cross-sectional view of the housing illustrated in FIG. 1 taken along line a-a of FIG. 1, illustrating an angled feed-through according to one embodiment of the present invention.

Turning to FIG. 2 where one feed-through 50 is shown in cross section and in greater detail, the connections 51 to the exterior of the housing 10 emerge from one side of the feed-through 50, and the connections 52 to the interior of the housing 10 emerge from the other side.

In the present embodiment and as shown in particular in FIG. 2, the feed-throughs 50, 50' are angled through a wall of the cavity 60, from the top side 20a of the body portion 20 to the bottom side 20b, to allow assembly from one side of the housing 10 while still creating a hermetic enclosure for the electrical assembly 70. The angling also allows the feed-throughs 50, 50' to be sufficiently long to form an effective hermetic seal, while minimizing the overall implant thickness. The length of the hermetic seal is may be important for embodiments in which the conductor is sealed in ceramic.

Standard biocompatible materials may be used for the various components of the device. Ideally, the body portion 20 and sealing flange 80 are made from a metal such as titanium, while the coil 40, electrode contacts and electrode wires are made from platinum or platinum/indium alloy, and the feed-throughs 50, 50' are made from an alumina based ceramic. Other biocompatible materials may however be used. For example, the body portion 20 and sealing flange 80 could be made from stainless steel, while the coil 40 is made from gold and the feed-through 50 is made from a zirconia based ceramic.

It certain embodiments of the present invention cavity 60 is shallow in depth relative to its surface area. This facilitates easy assembly, as it provides easy access for manually or automated operations. Further, it assists in minimizing the thickness of the housing 10.

Typically, the feed-throughs 50, 50' and associated components 30, 40 constrain the thickness of the implant. The angled feed-through 50, 50', combined with the single sided body portion 20 assists in allowing a thinner implant to be achieved. For example, for a specific cochlear implant with housing dimensions of approximately 20 mm×30 mm, a thickness of approximately 2.5 mm is achievable. An implant of this thickness is may be beneficial for implantation in children. While the skull of even small children is more than large enough in area to accommodate an implant, the curvature is much greater than for an adult, and accordingly a thickness of the order of approximately 6 mm (typical for current implants) results in a discernable bump under the skin.

Despite the reduced thickness realized through embodiments of the present invention, such embodiments still provide significant material and strength in the housing 10. For example, as discussed above, in certain embodiments the body portion 20 and sealing flange 80 may be formed from titanium. In such embodiments, there are a number of regions of the body portion 20 where the titanium is the full thickness of the body portion 20, shown for example in FIG. 2, and the body portion 20 will be rigidly attached to the titanium sealing flange 80 by laser welding (as will be further described below). This makes the construction extremely robust and results in high resistance to impact.

Figure 3:
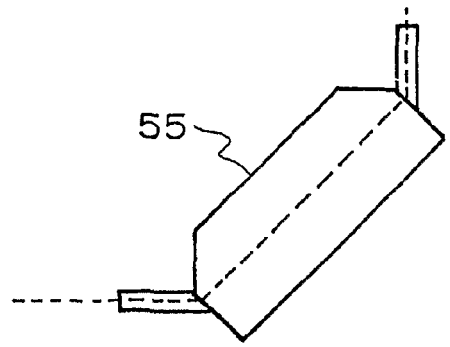
FIG. 3 is a side view of a tool used to make the feed-through shown in FIG. 2, according to one embodiment.
Figure 4:
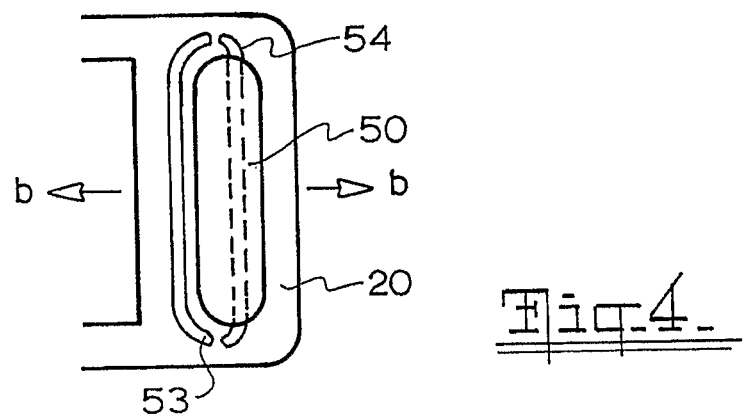
Figure 5:
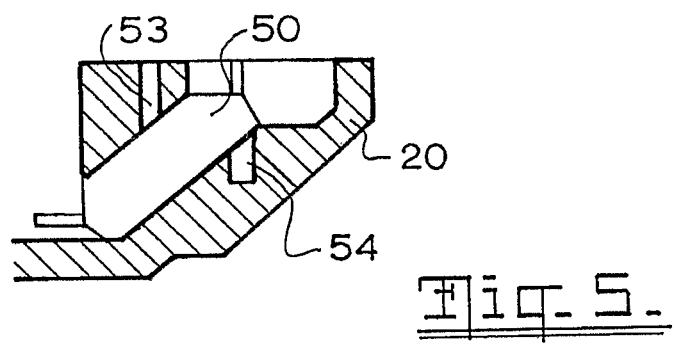
FIG. 5 is a cross-sectional view of the body portion of FIG. 4 taken along line b-b of FIG. 4.

An angled feed-through shape as in the present embodiment can be made such that it can still be molded on a simple split tool 55 as shown in FIG. 3. The construction of the ceramic feed-through is otherwise conventional, and will not be further described as it is well understood by those skilled in the art. As is conventional, the ceramic may be brazed to the titanium body portion 20, using any suitable technique to establish a suitable seal. The brazing could be controlled using, for example, capillary brazing. Suitable braze reservoirs 53, 54 are constructed in the body portion 20, as shown in FIGS. 4 and 5.

It will be appreciated that embodiments of the present invention may be applied to arrangements with a single feed-through, or to arrangements having two or more feed-throughs.

Figure 6:
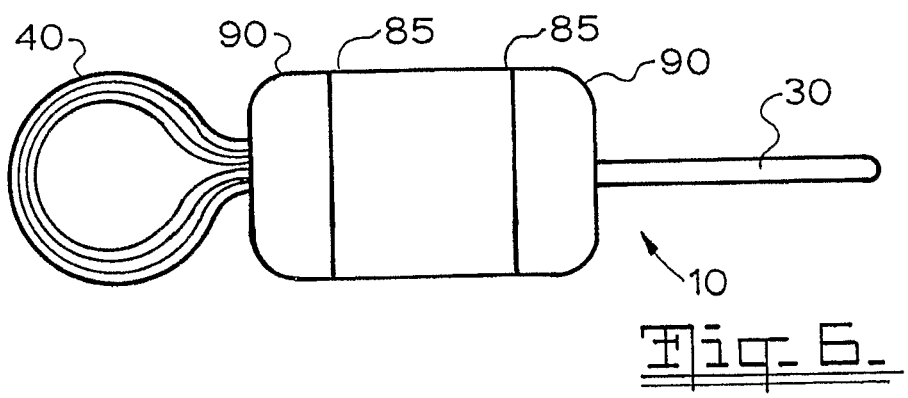
FIG. 6 is a top view of the housing, including both the body portion and the sealing flange, according to one embodiment of the present invention.
Figure 7:
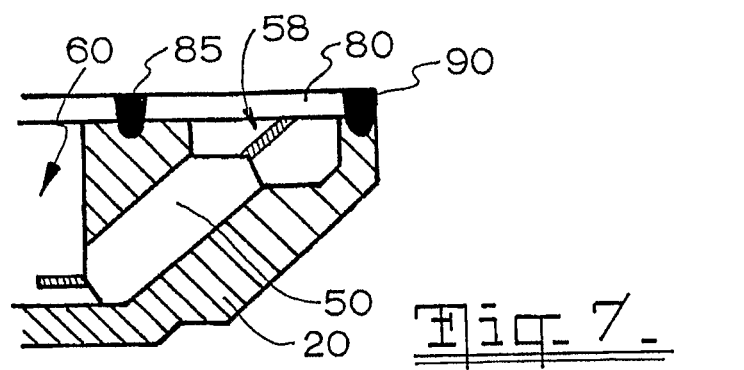
FIG. 7 is a partial cross-sectional view of the housing shown in FIG. 6 showing the weld positions for the sealing flange.

FIG. 6 shows a top view of the housing 10 of FIG. 1 with the sealing flange 80 (or top shell) attached. FIG. 7 shows a more details cross-sectional view of this arrangement. The top shell 80 is may be attached to the body portion 20 using laser welding at a number of points 85, 90 on the body portion 20. In particular, welding is performed around the outside of the body portion 20 indicated by reference 90, along with additional welds across the width of the body portion 20, as indicated by reference 85, to seal the central hermetic cavity 60.

Figure 8:
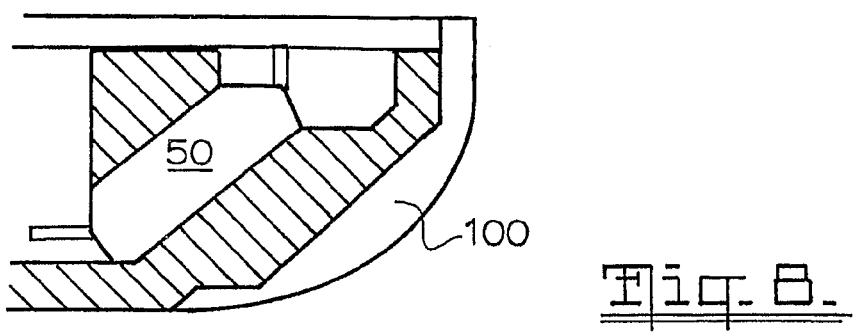
FIG. 8 is another partial cross-sectional view of the housing shown in FIG. 6 subsequent to overmolding.

Note that the channels 58 in certain embodiments are not sealed into the hermetic space, but are protected by the shell 80 and sealed by the silicone material as part of the overmolding process. Final overmolding is achieved using vacuum silicone molding similar to existing implants, to produce the final sealed housing 100 as shown in FIG. 8.

Figure 9:
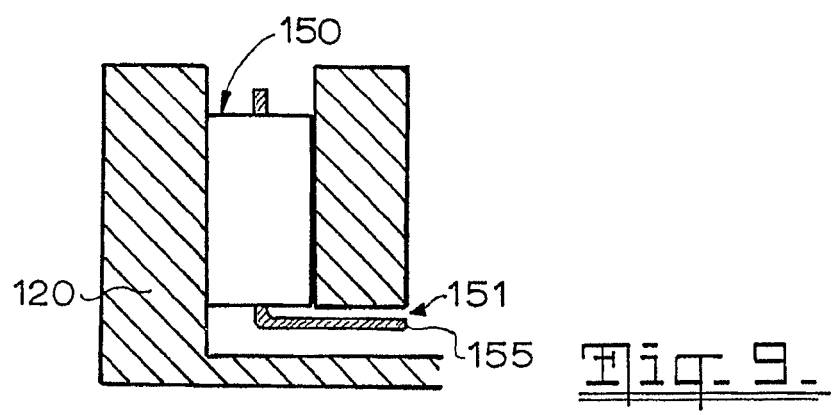
FIG. 9 is a cross-sectional view of a feed-through configuration in the body portion of a housing according to other embodiments of the present invention.
Figure 10:
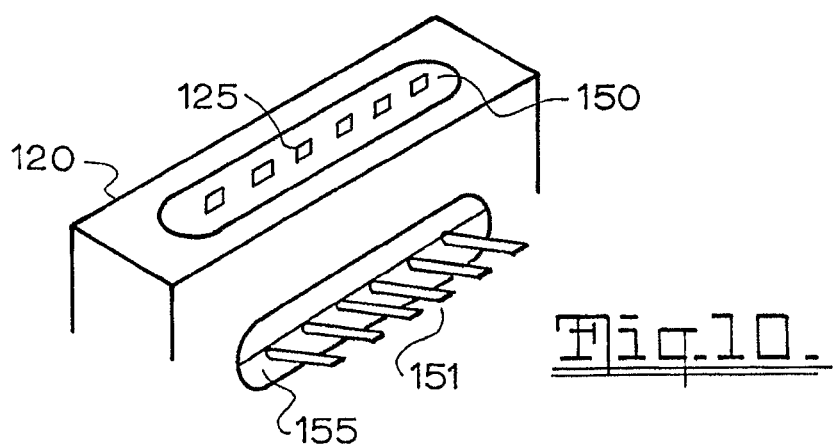
FIG. 10 is a perspective view of the feed-through configuration of FIG. 9.

FIGS. 9 to 13 illustrate an alternative embodiment of the housing, in which the housing wall is undercut. As can be seen in FIGS. 9 and 10, the feed-through 150 is generally parallel to the wall of the cavity 60, with the feed-through entry 125 for connectors being accessible from the top of the housing 120, as is the feed-through exit 151. The exit 151 of the feed-through 150 is formed in the housing wall 120 as an undercut portion to allow assembly from one side while still creating a hermetic enclosure for the electrical assembly (not shown in this view). The conductors 155 may be simply bent, as can be seen in FIG. 9, so as to pass into the interior of the housing 120.

Figure 11:
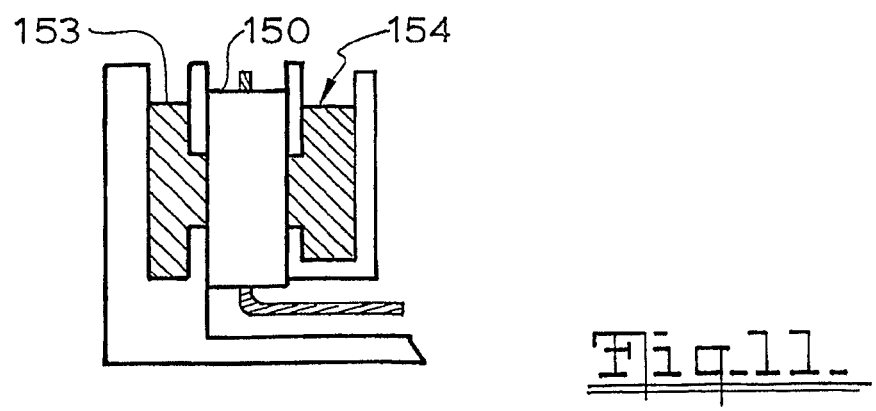
FIG. 11 is a cross-sectional view of the body portion with feed-through of FIG. 9 with suitable braze wells.
Figure 12:
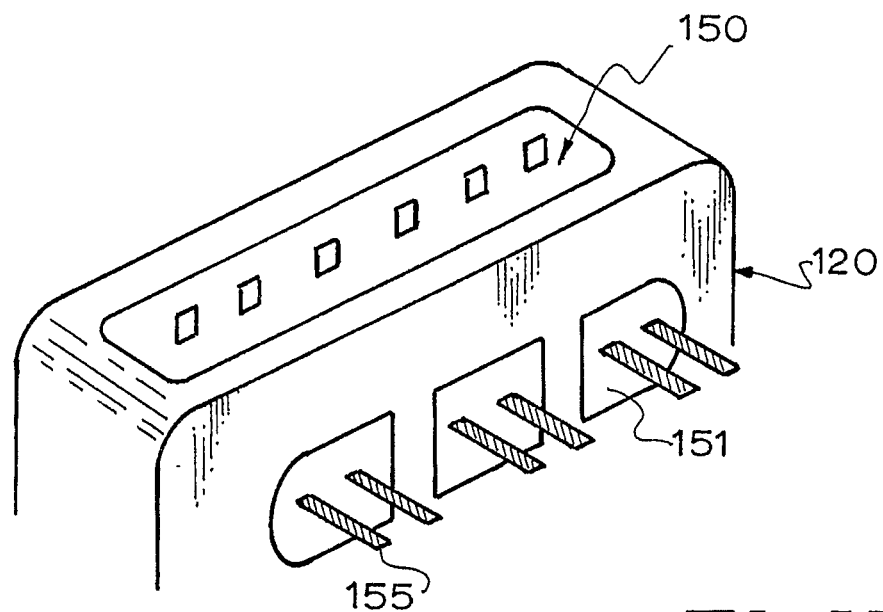
FIG. 12 is a perspective view of an alternative exit configuration of the feed-through configuration of FIG. 9.

In certain such embodiments, cavity 60 may be relatively shallow relative to the surface area. This facilitates easy assembly, as it provides easy access for manually or automated operations. Further, it assists in minimizing the thickness of the housing 120. As noted, the feed-through structure may be a constraint on how thin the implant as a whole may be manufactured. The vertical feed-through 150 used in this second implementation, combined with a single sided housing 120, assists in allowing a thinner implant to be achieved. Similar to the embodiments described above, significant material and strength in the housing 120 remains in the implementation of FIGS. 9-13. The strength according to these embodiments may be further improved by adding one or more pillars 152 to the undercut 151 shown in FIG. 10. This results in an undercut 151 as shown in FIG. 12.

An undercut 151 to the housing 120 can be machined from solid titanium using conventional techniques, and will not be further described as it is well understood by those skilled in the art. As is conventional, the ceramic feed-through 150 may be brazed to the titanium housing, using any suitable technique to establish a seal. Suitable braze reservoirs 153, 154 are shown in FIG. 11.

Figure 13:
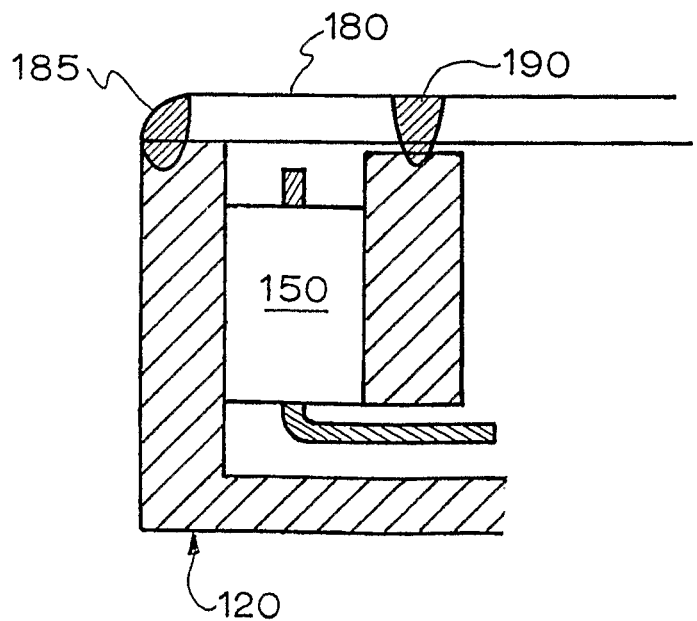
FIG. 13 is a partial cross-sectional view of the housing, including the body portion shown in FIG. 9 and the sealing flange, showing the weld positions for the sealing flange on the housing.

FIG. 13 illustrates feed-through 150 positioned in the housing 120 after brazing and sealing. Sealing flange 180 is attached at welding points 185, 190 to seal the enclosure after the electrical connections are completed. The assembly can then be overmolded, as described above.

Figures 14A, 14B:
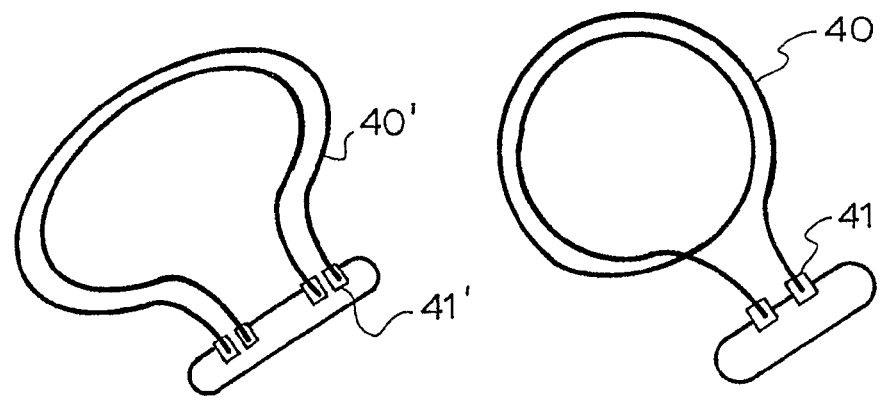
FIGS. 14a and 14b illustrate alternative feed-through attachments to the housing according to an embodiment of the present invention.

FIGS. 14a and 14b illustrate two alternative feed-through attachments to the housing. In FIG. 14a, two coils 40' are shown, requiring four exterior connection points 41' to the housing. In FIG. 14b, one coil 40 is used, requiring only two exterior connection points 41 to the housing.

Figure 15:
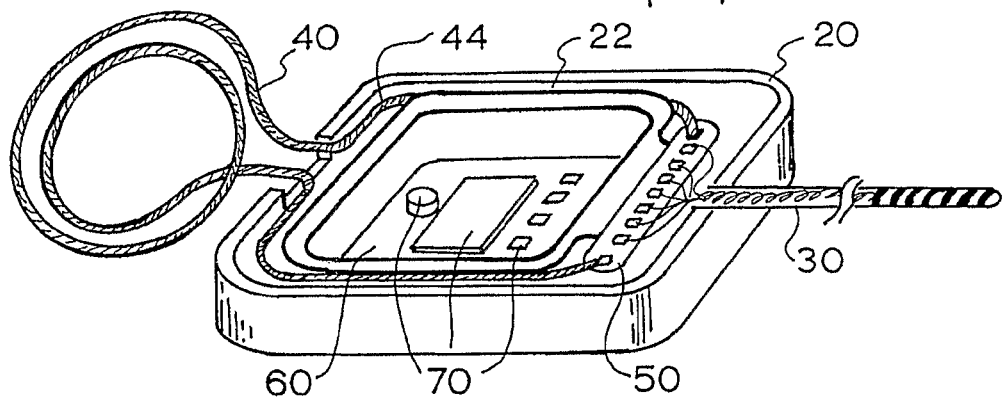
Figure 16:
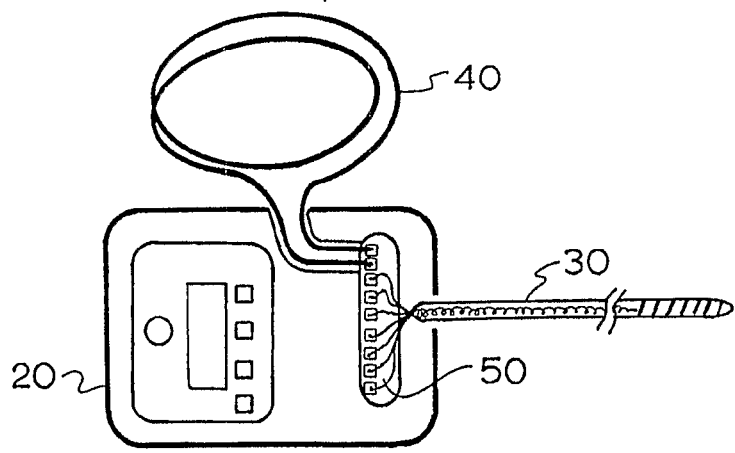

FIGS. 15 and 16 illustrate two alternative arrangements in which the coil 40 and the electrode array 30 can utilize the same feed-through 50. FIG. 15 illustrates coil 40 at the opposite side of the body portion 20 to the feed-through 50 with the coil connector 44 being contained in a channel 22 around the perimeter of the body portion 20 and fed to the feed-through 50. This method requires longer wiring and slightly increased weld complexity to the embodiments described above having two feed-throughs. FIG. 16 illustrates the coil 40 at ninety degrees to the feed-through 50. Again, this construction requires slightly increased wiring and weld complexity, but may be suitable for particular applications.

To further simplify assembly of the housing in accordance any of the above embodiments, the coil 40 and coil feed-through 50' can be assembled together, prior to insertion into, or assembly of, the housing. The coil 40 generally is made up of a carrier and an electrical conductor embedded in the carrier. The electrical conductor may be conveniently formed by punching it from a foil, which could be made for example from platinum, with a multi coil structure being formed by further folding the punched foil. Such a foil coil 40 may have a shape other than circular, and the technique may be implemented with connectors other than coils, e.g. electrode arrays.

Figure 17:
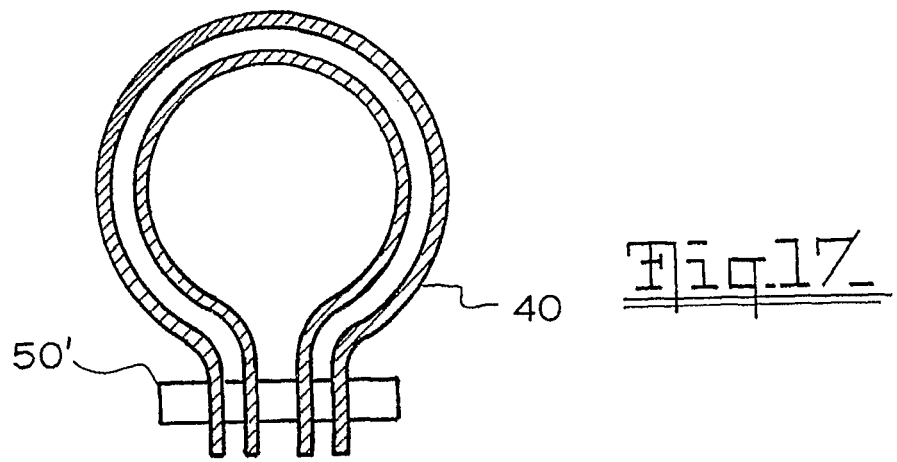
FIG. 17 is a perspective view of a coil and feed-through according to one embodiment of the present invention.

In certain embodiments, a powder injection molding (PIM) feed-through concept may be implemented. In such embodiments, the PIM feed-through allows feed-throughs to be molded around a platinum pin. Using both the foil coil 40' and the PIM feed-through technique, the coil 40 may be moulded straight onto the feed-through 50' as shown in FIG. 17, as opposed to a subsequent coil attachment process as shown in FIGS. 14a and 14b. This is performed as part of feed-through manufacture. Hence, in such an embodiment, the feed-through manufacturing process results in a combined coil-feed-through sub assembly. This sub assembly is brazed to the housing 10 as in other embodiments.

Figure 18:
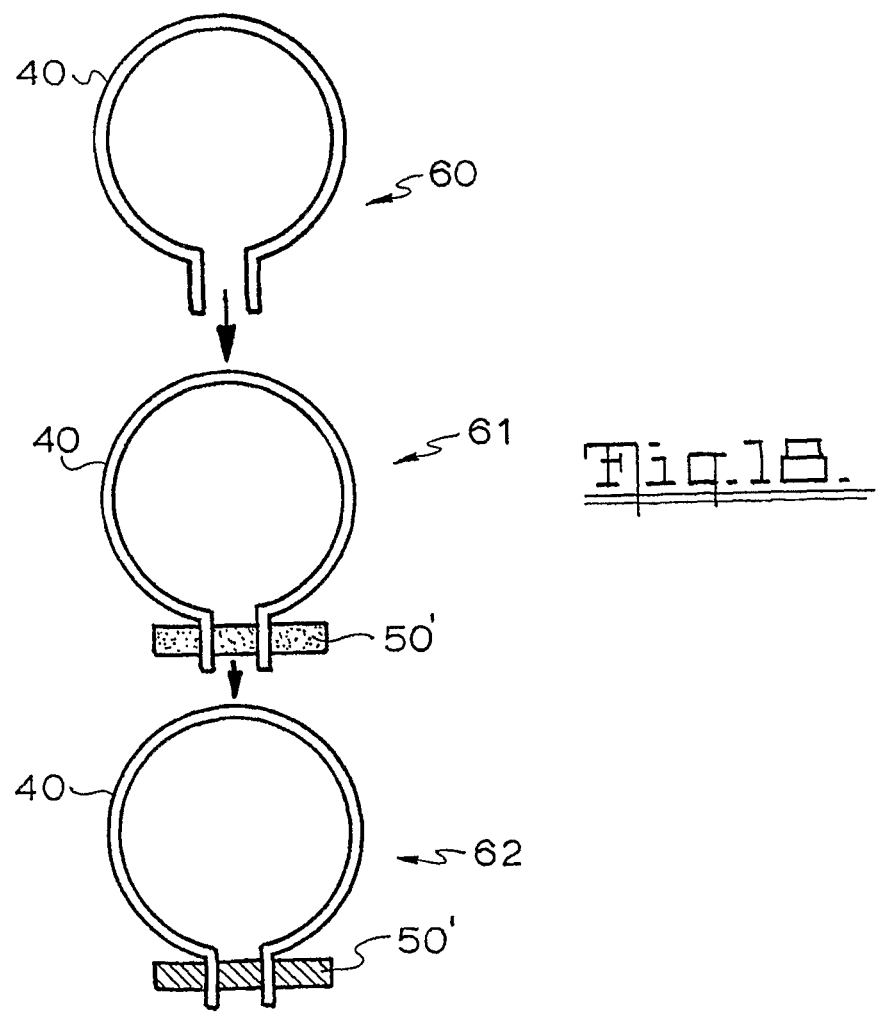
FIG. 18 shows an illustrative sequence for manufacturing a combined coil/feed-through component.

Referring to FIG. 18, a suitable process for forming the combined feed-through assembly is described. The coil 40 is first stamped from a foil of suitable metal, as indicated by step 60. Ceramic powder is then molded around the protruding legs of the foil coil 40, for example using a powder injection molding process, indicated as step 61. The ceramic is then subjected to the regular processes of ceramic manufacture, for example de-binding and sintering, to form a finished sub-assembly at step 62. It will be appreciated that as the coil 40 is typically formed from a platinum or platinum alloy, it can be readily subjected to the heating processes necessary for the ceramic.

In other embodiments the coil 40 may be attached to the feed-through 50' after each have been separately formed. The coil 40 may be formed using a foil coil, or a conventional coil, and then attached via welding/crimping or other suitable method. This coil/feed-through assembly could equally be used by any connector(s) and connector feed-through. As described above, the ceramic feed-through 50' may then be brazed to the titanium housing 10, using any suitable technique to establish a suitable seal.

Connections from the feed-through connection 50b to the electrical assembly 70 may be made using any available technologies such as soldering. However, in certain embodiments such connections may be made using an easily automated technique such as resistance welding or wire bonding.

A magnet is typically used to provide an attractive force to position an external coil which forms a transcutaneous link to the implant coil. To further simplify assembly, the magnet may be contained in the housing rather than with the exterior coil.

Figure 19:
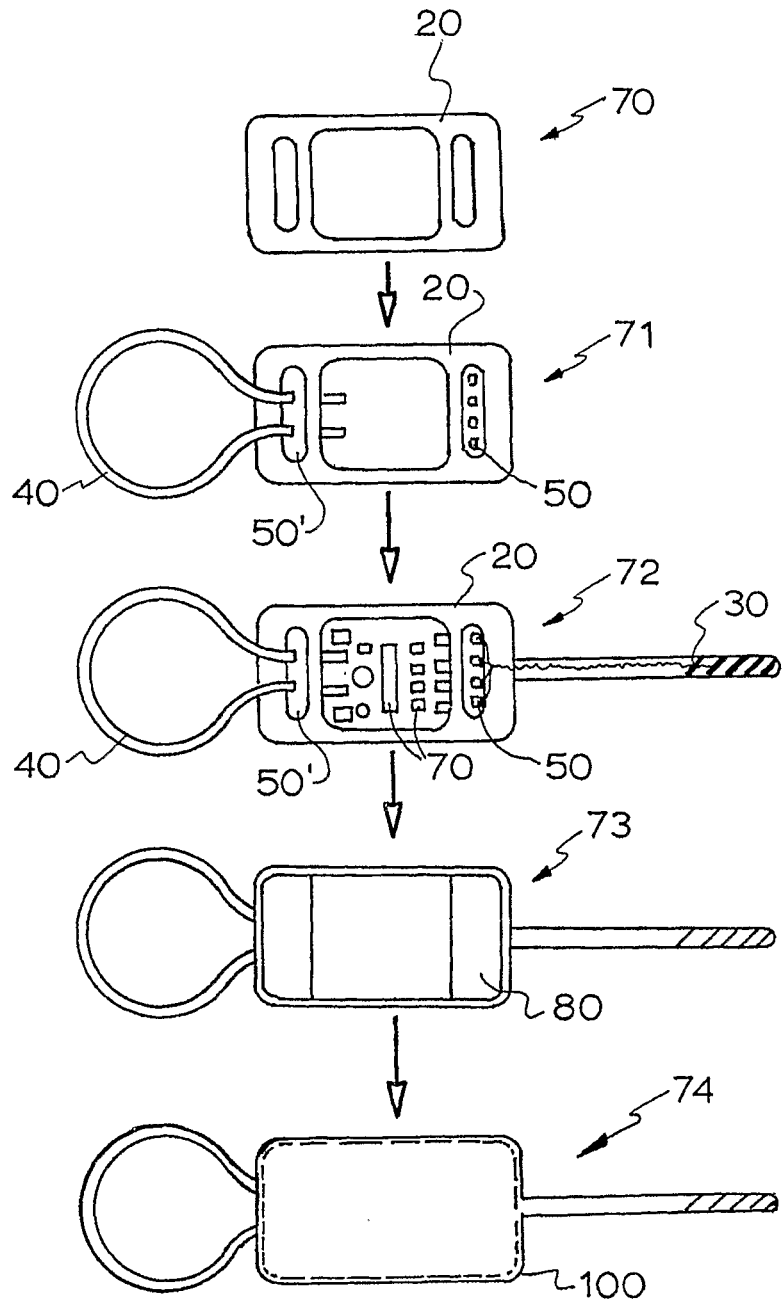
FIG. 19 shows an illustrative sequence of assembling the housing of embodiments of the present invention.

A suitable process for assembling a housing, such as that illustrated in FIG. 1 or FIG. 9, will now be described with reference to FIG. 19. It will be appreciated that is merely illustrative and the process may vary depending upon the device being manufactured.

At step 70, the body portion 20 and sealing flange 80 are formed in titanium, using conventional processes. A dispenser applies braze paste into the previously described reservoirs 53, 54 in the body portion 20. A "pick and place" machine inserts the feed-throughs 50, 50' into the cavities in the body portion 20. Preferably, the feed-through 50' is attached to the coil 40 prior to insertion into the cavity, forming a sub-assembly, per the method described above.

At step 71, the assembly is then placed into a furnace to melt the braze and seal the feed-throughs 50, 50' to the body portion 20. The "pick and place" machine then positions the electrical assembly 70 in the body portion 20, together with the magnet(s) noted above, and places the electrode array 30 (and coil 40 if not part of a sub-assembly) into position. A robotic welder then makes the necessary electrical connections.

In the case of the second embodiment shown in FIGS. 9 to 13, the feed-through 150 can be inserted vertically into the corresponding cavity, with otherwise similar processes.

At step 72, the "pick and place" machine places the top shell 80 into position. It is noted that the shell 80 covers the whole top surface of the body portion 20, but is welded so as to leave the feed-through connections outside the sealed cavity 60. The shell 80 accordingly acts as a sealing flange for the cavity 60 in the body portion 20. A robotic laser welder can be used to affix the top shell 80.

Finally, the housing 10 is subjected to an overmold procedure in which a sealing material encases the entire assembly. The sealing material may be any suitable biocompatible material, for example a silicone polymer. The assembly, as shown at step 74, is then complete.

As noted above, it would be understood that embodiments of the present invention are applicable to any type of medical device in which a feed-through arrangement is utilized to electrically connect components within a housing to components exterior to the housing. It will be further understood that the method described in FIG. 18 may be applied to differently designed housings, using different types of feed-throughs. Variations and additions, for example to the processes for forming and affixing the feed-through sub-assembly, are possible within the scope of the present invention.

The foregoing discussion is considered as illustrative only of the principles of the invention. Furthermore, since numerous modifications and changes will readily occur to those skilled in the art, it is not desired to limit the invention to the exact construction and operation shown and described, and accordingly, all suitable modifications and equivalents may be used, falling within the scope of the invention.
characteristics may be combined in any suitable manner in one or more combinations.

The invention described and claimed herein is not to be limited in scope by the specific embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All patents and publications discussed herein are incorporated in their entirety by reference thereto.

The invention claimed is:

1. A housing for an implantable device, the housing comprising:
   a body portion having a plurality of walls defining a cavity in which electronic components may be disposed, the cavity having an opening to an exterior of the housing on a first side of the body portion;
   a feed-through disposed in a first of the plurality of walls to provide an electrical connection through the first wall between the electronic components and the exterior of the device, the feed-through having interior and exterior connection points accessible during assembly of the device from the first side of the body portion; and
   a sealing flange operatively sealing the cavity so as to form a sealed housing.

2. The housing according to claim 1, wherein the cavity has shallow depth relative to the area defined by the cavity opening.

3. The housing according to claim 1, wherein at least part of the feed through is generally parallel to the first wall of the cavity, and wherein the first wall comprises:
   an undercut portion adjoining the cavity so that the interior connection is accessible during manufacture through the cavity.

4. The housing according to claim 1, wherein at least part of the feed-through passes at an angle through the first wall of the cavity.

5. The housing according to claim 1, further comprising:
   a second feed-through disposed in one of said plurality of walls and having interior and exterior connection points accessible during assembly of the device from the first side of the body portion.

6. The housing according to claim 5, wherein the housing contains components of an implantable hearing prosthesis comprising a stimulation component and a coil, and wherein at least one of the exterior connection points of the feed-through disposed in the first wall is connectable to the coil, and wherein at least one of the exterior connection points of the second feed-through is connectable to the stimulation component.

7. The housing according to claim 5, wherein the second feed-through is disposed in second of said plurality of walls of the body portion.

8. The housing according to claim 1, wherein at least one of the external electrical connection points of the feed-through is retained in a channel on a surface of the first side of the body portion.

9. The housing according to claim 1, wherein at least one of the exterior connection points is integral with the feed-through.

10. The housing according to claim 1, wherein one or more of the exterior connection points are connectable to exterior components selected from the group comprising a coil, an electrode array, or an electrical connection component.

11. A method of forming a sealed housing for an implantable device comprising:
    providing a body portion having a plurality of walls defining a cavity, the cavity having an opening to an exterior of the housing on a first side of the body portion;
    inserting the electronic components into said cavity;
    positioning at least one feed-through in a first of the plurality of walls to provide an electrical connection through the first wall between the electrical components and the exterior of the device, the feed-through having interior and exterior connection points accessible during manufacture of the device from the first side of the body portion; and
    attaching a sealing flange over the opening of the cavity so as to form a sealed housing.

12. The method according to claim 11, wherein providing the body portion further comprises:
    providing a body portion having a cavity that has a shallow depth relative to the area defined by the cavity opening.

13. The method according to claim 11, wherein the first wall comprises an undercut portion adjoining the cavity, and wherein positioning at least one feed-through in the first wall further comprises:
    positioning the feed-through such that at least a part of the feed-through is generally parallel to a wall of the cavity and such that the interior connection points are accessible in the undercut portion from the cavity during assembly.

14. The method according to claim 11, wherein positioning at least one feed-through in the first wall further comprises:
    positioning the feed-through such that at least a part of the feed-through passes at an angle through the first wall of the cavity.

15. The method according to claim 11, further comprising:
    positioning a second feed-through in one of the plurality of walls of the cavity, the second feed-through having interior and exterior connection points accessible during assembly of the device from the first side of the body portion.

16. The method according to claim 15, wherein the implantable device is a hearing prosthesis comprising a coil and a stimulation component, and wherein the method further comprises:
    connecting at least one of the exterior connection points of the feed-through disposed in the first wall to the coil, and
    connecting at least one of the exterior connection points of the second feed-through to the stimulation component.

17. The method according to claim 11, further comprising:
    connecting one or more of the exterior connection points of the feed-through to an exterior component prior to positioning the feed-through into the body portion.

18. The method according to claim 11, further comprising:
    forming a feed-through assembly exterior to the housing, the feed-through assembly including the feed-through and an exterior component connected to one or more of the exterior connection points; and inserting the feed-through assembly into the housing.

19. The method according to claim 17, wherein the exterior component is selected from the group comprising a coil, an electrode array, or an electrical connection component.

20. The method according to claim 19, wherein the coil, electrode array or electrical connection component includes a conductor, and wherein the method further comprises:
    forming the conductor by stamping from a metal foil.

21. The method according to claim 11, metal, and wherein the feed-through is formed of ceramic, and wherein the method further comprising:
    affixing the ceramic feed-through to the first wall via a brazing process.

22. A housing for an implantable device, the housing comprising:
    a body portion having a plurality of walls defining a cavity in which electronic components may be disposed, the cavity having an opening to an exterior of the housing on one of a top side or a bottom side of the body portion;
    a feed-through disposed in a first of the plurality of walls to provide an electrical connection through the first wall between the electronic components and the exterior of the housing, the feed-through having interior and exterior connection points both of which are accessible from the side of the body portion including the opening to the exterior of the housing; and a sealing flange operatively sealing the cavity so as to form a sealed housing.

23. The housing of claim 22, wherein the feed-through is disposed in the first wall at a non-perpendicular angle relative to the first wall.

24. The housing of claim 22, wherein the feed-through is disposed in the first wall at a non-perpendicular angle relative to at least one of a top surface and a bottom surface of the body portion.

25. The housing of claim 22, wherein the feed-through extends through the first wall between two surfaces of the first wall that are not parallel.

26. The housing of claim 25, wherein the two surfaces of the first wall are angled relative to each other.

27. The housing of claim 26, wherein the two surfaces of the first wall are generally perpendicular to each other.

28. The housing of claim 22, wherein at least part of the feed-through is generally parallel to the first wall of the cavity, and wherein the first wall comprises:

an undercut portion forming an opening connecting to the cavity so that the interior connection is accessible during manufacture through the cavity.

29. The housing of claim 28, wherein the undercut portion is angled relative to the part of the feed-through that is generally parallel to the first wall.

30. The housing of claim 29, wherein the undercut portion is generally perpendicular to the part of the feed-through that is generally parallel to the first wall.

* * * * *